US012751468B2

(12) United States Patent
Rudie et al.

(10) Patent No.: US 12,751,468 B2

(45) **Date of Patent: *Oct. 6, 2026**

(54) METHOD FOR PROVIDING PROTEINACEOUS COMPOSITION

(71) Applicant: Michael Foods, Inc., Minnetonka, MN (US)

(72) Inventors: Noel G. Rudie, Gaylord, MN (US); Alicia Stube, Gaylord, MN (US); Daniel L. Vance, Gaylord, MN (US); Todd D. Bohman, Gaylord, MN (US)

(73) Assignee: Michael Foods, Inc., Minnetonka, MN (US)

( * ) Notice: Subject to any disclaimer, the term of this patent is extended or adjusted under 35 U.S.C. 154(b) by 257 days.

This patent is subject to a terminal disclaimer.

(21) Appl. No.: 18/585,703

(22) Filed: Feb. 23, 2024

(65) Prior Publication Data

US 2024/0188585 A1 Jun. 13, 2024

Related U.S. Application Data

(63) Continuation of application No. 16/198,851, filed on Nov. 22, 2018, now Pat. No. 11,937,618.

(60) Provisional application No. 62/590,196, filed on Nov. 22, 2017.

(51) Int. Cl.

| | |
|---|---|
| ***A23J 1/09*** | (2006.01) |
| ***A23B 5/035*** | (2006.01) |
| ***A23J 1/08*** | (2006.01) |
| ***A23J 3/04*** | (2006.01) |
| ***A23L 15/00*** | (2026.01) |
| ***C07K 1/34*** | (2006.01) |

(52) U.S. Cl.

CPC ................ *A23J 1/09* (2013.01); *A23B 5/035* (2013.01); *A23J 1/08* (2013.01); *A23J 3/04* (2013.01); *A23L 15/00* (2016.08); *C07K 1/34* (2013.01); *A23V 2250/5428* (2013.01); *A23V 2300/34* (2013.01)

(58) Field of Classification Search

CPC .... A23J 1/09; A23J 1/08; A23L 15/00; C07K 1/34; A23V 2250/5428

See application file for complete search history.

(56) References Cited

U.S. PATENT DOCUMENTS

| | | | |
|---|---|---|---|
| 4,486,413 | A | 12/1984 | Weisenberger et al. |
| 6,287,623 | B1 | 9/2001 | Nakayama et al. |
| 8,273,394 | B2 | 9/2012 | Watabave |
| 8,642,038 | B2 | 2/2014 | Mason |
| 8,916,156 | B2 | 12/2014 | Mason |
| 2004/0161514 | A1 | 8/2004 | Akashe et al. |
| 2005/0079259 | A1 | 4/2005 | Gao et al. |
| 2005/0233053 | A1 | 10/2005 | Shen et al. |
| 2005/0276904 | A1 | 12/2005 | Brown et al. |
| 2008/0003335 | A1 | 1/2008 | Singh et al. |
| 2008/0226805 | A1 | 9/2008 | Watatanabe et al. |
| 2009/0304863 | A1 | 12/2009 | Okuyama et al. |
| 2012/0046449 | A1 | 2/2012 | Green et al. |
| 2013/0129900 | A1 | 5/2013 | Sridhar et al. |
| 2014/0066596 | A1 | 3/2014 | Mason |
| 2015/0094453 | A1 | 4/2015 | Mason |
| 2017/0223989 | A1 | 8/2017 | Jimenez et al. |

FOREIGN PATENT DOCUMENTS

| | | |
|---|---|---|
| CA | 2803101 | 1/2012 |
| EP | 2926674 | 11/2016 |
| WO | WO 2017136119 | 8/2017 |
| WO | WO 2020/206399 | 10/2020 |

OTHER PUBLICATIONS

Wu, Z. et al. Food Bioprocess. Technol. (2015), vol. 8, pp. 148-157 (published online on Aug. 15, 2014) (Year: 2014).*

"PH stability", *The Incredible Egg*, Sep. 29, 2022, https://www.incredibleegg.org/professionals/manufactures/real-egg-funcionality/ph-stability.

"Protein Concentration and Diafiltration by tangential flow filtration", *Millipore Corporation*, 2003.

Abeyrathne, E.D.N.S., et al. "Egg white proteins and their potential use in food processing or as nutraceutical and pharmaceutical agents—A review.", *Poultry Science*, pp. 3292-3299, 2013.

Froning et al. "Effect of ultrafiltration and reverse osmosis on the composition and functional properties of egg white", *Poultry Science*, vol. 66, No. 7, pp. 1168-1173, 1987.

* cited by examiner

*Primary Examiner* — James H Alstrum-Acevedo

(74) *Attorney, Agent, or Firm* — Norton Rose Fulbright US LLP

(57) ABSTRACT

A protein-rich composition can be provided from egg albumen via a process that involves diafiltering with purified water an egg albumen concentrate. Collected retentate from the diafiltration step constitutes a protein-rich composition which, on a dry basis, can include less than 1% (w/w) lipids. The composition can be spray dried to a protein isolate solid which is substantially free of sugars.

20 Claims, No Drawings

METHOD FOR PROVIDING PROTEINACEOUS COMPOSITION

CROSS-REFERENCE TO RELATED APPLICATIONS

This application is a continuation of U.S. application Ser. No. 16/198,851, filed Nov. 22, 2018, which claims the benefit of U.S. Provisional Patent Application No. 62/590,196, filed Nov. 22, 2017, each of which are incorporated herein by reference in their entireties.

BACKGROUND INFORMATION

Avian eggs, particularly hen eggs, have been a food staple for centuries. Over time, different uses have manifested for egg whites and egg yolks.

Egg white, also known as albumen, is the clear, alkaline liquid portion of the egg surrounding the egg yolk. It constitutes roughly two-thirds of a chicken egg by weight.

Egg white includes 10-12% (w/w) proteins as well as trace amounts of minerals, fats, vitamins, and carbohydrates carried in water. Slightly more than half of an egg's protein content, yet very little of its fat content and none of its cholesterol, is contained in the egg white.

Nearly 150 proteins have been identified in egg white including, for example, ovalbumin, ovotransferrin, and ovomucoid, as well as less abundant proteins such as ovoglobulin G2 and G3, ovomucin, lysozyme, ovoinhibitor, ovoglycoprotein, flavoprotein, and ovo-macroglobulin.

The fact that egg white is high in protein yet low in fat and cholesterol makes it a valuable commodity; however, those desirable proteins are carried in a large amount of water, typically 87-90% (w/w) of the overall albumen. Isolating the proteins from albumen has proven to be a not insignificant task, one which often requires large amounts of time, effort and energy.

Isolated, purified proteins, usually in powdered form, are widely used as nutritional supplements. Protein powders typically are provided from whey, soy, or casein, with whey constituting the source for about 90% of commercially available powders.

Powdered proteins from eggs, particularly egg albumen, are not nearly as common. This is true despite being a favored supplement before the other types of powdered proteins became widely available in the 1990s. The protein blend provided from albumen is considered to be superior in many ways, including taste, and is lactose-free, very low in carbohydrates, cholesterol free, and rich in desirable vitamins.

Spray dried egg whites, a commodity product often used in baking, are traditionally 80% (w/w) protein on a dry basis. That weight percentage of protein is not generally considered high enough for this product to be considered commercially competitive with the powdered proteins discussed above. For example, a protein bar manufacturer wishing to market a 60 g protein bar having 20 g protein would need to dedicate 37% of those 60 g to a 90% powder but 42% of that same mass to a 80% powder.

An efficient, commercial scale process that can reduce the water content of albumen and/or provide a protein-rich composition from albumen therefore is highly desirable.

SUMMARY

The present method advantageously can be used to provide a protein-rich composition from egg albumen. The method involves providing a concentrate by removing water from egg albumen. The concentrate is diafiltered with purified water. Collected retentate from the diafiltration step constitutes a protein-rich composition which, on a dry basis, can include less than 1% (w/w) lipids.

Removal of water to form a concentrate can be accomplished in a single step or in multiple steps.

The diafiltration step(s) can employ a membrane having a nominal molecular weight cutoff (MWCO) of from 1 to 30 kiloDaltons (kDa), with MWCO referring to the approximate molecular weight (MW) of a dilute globular solute (such as a typical protein) which is 90% retained by a given membrane.

The electrical conductance of the filtrate (permeate) from the diafiltration step(s) can be monitored so as to provide an indication of diafiltration endpoint. In some embodiments, when the conductance of the filtrate reaches a target value, diafiltration can be halted. In some embodiments, the target value can be 5 mS or less.

The retentate optionally can be pasteurized.

The retentate also or alternatively can be spray dried, with this additional step permitting provision of a protein isolate. The isolate optionally can be pasteurized.

The method optionally can involve instantizing the protein isolate.

Advantageously, the method can provide a protein-rich composition which includes proteins that have not been fermented. This is desirable because fermentation often produces chemical compounds that have odors or flavors that impact the organoleptic properties of the protein-rich composition and protein isolate. The present process yields a de-sugared protein-rich composition and protein isolate that a clean flavor profile, which is more desirable than that of whey-derived protein powders.

The more detailed description that follows provides additional details which explain and exemplify the aforedescribed method. The appended claims define the inventions in which exclusive rights are claimed, and they are not intended to be limited to particular embodiments shown and described, from which ordinarily skilled artisans can envision variations and additional aspects.

DETAILED DESCRIPTION OF ILLUSTRATIVE EMBODIMENTS

Methods according to the present invention involve the use of egg albumen, yielding sequentially a concentrate, a retentate, and, if dried, a powder. The latter does not qualify as "dried egg white," differing by at least 20% from U.S. Department of Agriculture (USDA) standards for that product.

The albumen starting material can be collected from whole eggs or be reconstituted from a powder. Commercial processes and equipment for separating whole eggs or reconstituting powdered egg whites are widely available.

The albumen employed in the process optionally can be pasteurized. Pasteurization has not been found to significantly impact necessary conditions or efficiency of the process.

Raw egg white is a preferred starting material because of the large number or percentage of proteins which have not been denatured due to exposure to heat.

Although possible to provide the aforementioned concentrate using just one or more diafiltration steps, commercial scale efficiencies argue for removing at least some of the water in the albumen prior to diafiltration.

Water removal can be accomplished in a single step (i.e., using a single technique) or in a series of steps, employing multiple techniques. Processes which minimize the amount of albumen proteins lost, particularly if the loss is somewhat selective with respect to type of protein, are preferred. Reverse osmosis constitutes an exemplary water removal process.

The water removal step typically is performed until at least 25%, at least 30%, at least 33%, at least 35%, at least 40%, at least 45% or even ~50% (all v/v) water has been removed from the albumen.

The product of this step is referred to herein as a concentrate. While the protein content of albumen generally is on the order of 10-12% (w/w), the protein content of the concentrate is at least 15%, commonly at least 17.5%, and typically at least 20% (all w/w). The protein content of the concentrate often is from 20-25% (w/w).

The concentrate is treated so as to enrich the proportion of proteins relative to other non-aqueous compounds. Amounts of small molecule compounds (e.g., carbohydrates including sugars) and ions (e.g., NaCl) are thereby reduced. (Removal of inorganic compounds sometimes is referred to as "deashing.")

The foregoing can be accomplished with one or more filtration sub-processes, performed in parallel or sequentially.

The filtration sub-process(es) typically employ a membrane having a MWCO below that which would permit passage of significant proteins; the most abundant egg white proteins have MWs of at least ~13 kDa, so employing a membrane with a MWCO higher than that risks loss of significant percentages of the smallest of those proteins.) Membranes having a MWCO of from 1 to 30 kDa typically are employed, with ultrafiltration (UF) membranes having a MWCO of at least 3 kDa, particularly those having a MWCO of at least 5 kDa or even at least 7 kDa, being preferred.

UF membranes having a MWCO of 10±2.5 kDa are particularly preferred. This MWCO range is in contrast to the recommendations of membrane manufacturers. For example, Pall Corporation recommends use of a UF membrane having a MWCO that is 3 to 6 times smaller than the MW of the protein(s) targeted for retention. Using the ~13 kDa value from the preceding paragraph, this would translate into selection of a membrane with a MWCO of from ~2 to ~4 kDa.

Filtration processes involving tangential rather than normal flow operation can be preferred for operational efficiency reasons.

Because a primary goal of this step is to reduce the amount of small molecule compounds and ions, those filtration techniques which do not reduce the volume of the concentrate can be employed. Accordingly, diafiltration constitutes an exemplary filtration technique. Diafiltration can be performed continuously (where a constant volume is maintained) or discontinuously, for example in a batch process.

The so-called diafiltration buffer used to replace the volume of filtrate passing through the membrane can be purified water, i.e., water having undergone a treatment such as reverse osmosis, distillation or deionization. In some examples, each diafiltration step is performed with less than 10, often with from ~1 to 7.5, and typically with from 2 to 6 volumes of diafiltration buffer.

In a preferred embodiment, increasing the proportion of proteins relative to other non-aqueous compounds can be accomplished in a single diafiltration step employing a UF membrane of the type described above.

Regardless of whether the protein enrichment involves one or more filtration sub-processes, the overall effect is to greatly reduce the amount of non-proteinaceous materials. This effect can be measured or determined in a variety of ways, including using a rapid solids method, such as microwave drying, to determine when a target endpoint is reached. For example, the last such filtration step might be deemed to be complete when its filtrate is determined to have a total solids content of, e.g., 10%, 8%, 6%, 4% or 2%.

A preferred technique for monitoring enrichment progress is to measure electrical conductance of the filtrate from each such filtration (with, for example, a conductivity meter). The electrical conductance of a filtrate decreases as the amount of ionic compounds in the filtered concentrate is depleted. When a given filtrate's conductance drops below a certain target, that particular filtration can be concluded, either manually or automatically.

Regardless of whether the protein enrichment involves one or more filtration sub-processes, the final filtration's filtrate can have a target conductance value of no more than 5 mS, e.g., no more than 4.5, 4, 3.5, 3.2, or 3 mS.

The retentate of the filtration process(es) is recovered. In the paragraphs that follow, this product is referred to as a protein-rich composition.

Advantageously, neither the protein rich composition nor a protein isolate provided therefrom requires pH adjustment prior to drying and/or subsequent processing.

The protein-rich composition can have a protein content that is about the same or about 5-10% less than that of the concentrate; for example, a concentrate having a protein content of 22% (w/w) might yield a protein-rich composition having a protein content of 20-21% (w/w).

Advantageously, the protein-rich composition is substantially free of lipids. A protein-rich composition product of the process, on a dry basis (i.e., considering solids only), typically includes less than 1%, commonly less than 0.75%, often less than 0.5%, occasionally less than 0.25%, and even less than 0.1% lipids (with all foregoing percentages being w/w), as determined by, for example, acid hydrolysis, rapid fat analysis, or the like.

None of the steps involved in the aforedescribed process need to be conducted at supra- or sub-ambient temperatures, although the process typically is performed at temperatures in the range of 0° to 35° C., with preferred maximum temperatures being on the order of no more than 30° C., no more than 27.5° C., no more than 25° C., no more than 22.5° C., or even ~20° C.

The protein-rich composition itself can be packaged and sold. The composition optionally can be pasteurized prior to or after packaging.

Commonly, however, the composition is converted to a free flowing solid. Doing so reduces the volume and weight of the product to be shipped, as well as provides a protein-rich isolate in a convenient, commercially desirable form.

Preferred solids are powders, which can be provided by pulse combustion drying or, more commonly, spray drying techniques. Equipment and conditions are familiar to ordinarily skilled artisans and, accordingly, are not described here.

Less preferred are techniques which provide protein isolates other than free flowing powders. For example, lyophilization typically yields non-free flowing solids while drum drying typically yields flaky solids.

Advantageously, protein isolate solids resulting from drying a protein-rich composition are substantially free of sugars (i.e., meeting regulatory standards to be listed as having 0 g sugars). Standard analytical techniques such as HPLC typically cannot detect glucose in protein-rich compositions provided according to the present method, as well as in solids provided therefrom. This is true even though the process can be performed without employing a bacterial or enzymatic de-sugaring processes, e.g., fermentation such as by addition of yeast or by an enzymatic reaction with, for example, glucose oxidase.

Many of the small molecules and ions removed during the filtration process(es) can stimulate taste buds. Their removal means that a protein isolate provided according to the present method typically is considered to have less overall flavor (including less "egg flavor") and to be less salty than dried egg white.

In addition to the foregoing, a protein isolate provided according to the present method has a different ratio of proteins than similar isolates provided from soy or whey. In Table 1 below, the soy numbers are from the USDA nutrient database active as of original date of filing), while the whey numbers are from a product bulleting for Hilmar™ 9000 whey protein isolate. The egg values are from analytical testing on a protein isolate prepared according to the afore-described method.

TABLE 1 protein comparison (all values in g)

| | Soy | Whey | Egg |
|---|---|---|---|
| Alanine | 3.6 | 4.9 | 5.2 |
| Arginine | 6.7 | 2.0 | 5.1 |
| Aspartic acid | 10.2 | 10.2 | 9.2 |
| Cysteine | 1.0 | 2.3 | 3.1 |
| Glutamic acid | 17.5 | 16.2 | 11.7 |
| Glycine | 3.6 | 1.5 | 3.2 |
| Histidine* | 2.3 | 1.5 | 2.1 |
| Isoleucine*^ | 4.3 | 6.4 | 4.7 |
| Leucine*^ | 6.8 | 9.7 | 7.7 |
| Lysine* | 5.3 | 9.3 | 6.7 |
| Methionine* | 1.1 | 2.1 | 3.4 |
| Phenylalanine* | 4.6 | 2.9 | 5.2 |
| Proline | 5.0 | 5.6 | 3.2 |
| Serine | 4.6 | 4.3 | 3.6 |
| Threonine* | 3.1 | 6.6 | 3.3 |
| Tryptophan* | 1.1 | 1.9 | 1.1 |
| Tyrosine | 3.2 | 2.7 | 2.7 |
| Valine*^ | 4.1 | 5.2 | 6.0 |

*essential amino acid

^branched chain amino acid

If desired, the protein isolate solid can be dry pasteurized prior to use or packaging.

The protein isolate, particularly a powder, can be instantized. For example, addition of soy or sunflower lecithin can assist in re-solubilizing the solid when it is mixed with a liquid prior to use.

The protein isolate, particularly a solid in powder form, can be used in the same manner as other protein powders, yet provide food products that have a more neutral flavor than soy or whey. For example, some baked goods made with a protein-rich composition or protein isolate can have textural properties similar to those of dried egg whites. Such baked goods accordingly can have acceptable organoleptic, particularly taste and mouthfeel, characteristics while having multifold protein concentrations relative to standard baked goods. Other baked goods can have different yet acceptable mouthfeel properties, while still having a multifold increase in protein concentration.

The foregoing description has employed certain terms and phrases for the sake of brevity, clarity, and ease of understanding; no unnecessary limitations are to be implied therefrom because such terms are used for descriptive purposes and are intended to be broadly construed. The relevant portion(s) of any patent or publication specifically mentioned in the foregoing description is or are incorporated herein by reference.

The foregoing compositions and methods have been presented by way of example only. Certain features of the described compositions and methods may have been described in connection with only one or a few such compositions or methods, but they should be considered as being useful in other such compositions or methods unless their structure or use is incapable of adaptation for such additional use. Also contemplated are combinations of features described in isolation.

That which is claimed is:

1. A method for providing a protein-enriched composition from egg albumen, the method comprising:

a) providing an egg albumen concentrate by removing at least 25% (v/v) of water from the egg albumen;

b) diafiltering the egg albumen concentrate; and c) providing a protein-enriched composition by collecting a retentate from step (b), wherein the egg albumen concentrate of steps (a) and (b) and the protein-enriched composition of step (c) are not pH-adjusted prior to subsequent processing.

2. The method of claim 1, wherein at least 33% (v/v) of water is removed from the egg albumen.

3. The method of claim 1, wherein water is removed from the egg albumen using reverse osmosis.

4. The method of claim 1, wherein the egg albumen concentrate has a protein content of greater than or equal to 15%.

5. The method of claim 4, wherein the egg albumen concentrate has a protein content of greater than or equal to 20%.

6. The method of claim 1, wherein the egg albumen concentrate is diafiltered with purified water and an ultrafiltration membrane having a nominal molecular weight cutoff of greater than or equal to 7 kDa.

7. The method of claim 1, wherein the diafiltration is performed with from about 1 to about 7.5 volumes of diafiltration buffer relative to the volume of the egg albumen concentrate.

8. The method of claim 1, wherein the retentate has an electrical conductance of less than or equal to 5 mS.

9. The method of claim 8, wherein the retentate has an electrical conductance of less than or equal to 3 mS.

10. The method of claim 1, wherein the protein-enriched composition includes, on a dry basis, less than 1% (w/w) lipids.

11. The method of claim 1, wherein the protein-enriched composition includes, on a dry basis, less than 0.5% (w/w) lipids.

12. The method of claim 1, wherein the protein-enriched composition is substantially free of sugars.

13. The method of claim 12, wherein the protein-enriched composition that is substantially free of sugars is provided without the use of fermentative organisms or enzymatic de-sugaring agents.

14. The method of claim 1, further comprising pasteurizing the protein-enriched composition.

15. The method of claim 14, further comprising providing a solid protein-enriched composition by spray drying the protein-enriched composition.

16. The method of claim 14, further comprising providing a solid protein-enriched composition by pulse combustion drying the protein-enriched composition.

17. The method of claim 14, further comprising providing a solid protein-enriched composition by spray drying the protein-enriched composition.

18. The method of claim 17, further comprising pasteurizing the solid protein-enriched composition.

19. The method of claim 17, wherein the solid protein-enriched composition is a free-flowing powder.

20. The method of claim 17, further comprising instantizing the powder.

* * * * *